United States Patent [19]

Marlett

[11] Patent Number: 5,045,244
[45] Date of Patent: Sep. 3, 1991

[54] PREPARATION OF METAL HALIDE-AMINE COMPLEXES

[75] Inventor: Everett M. Marlett, Baton Rouge, La.

[73] Assignee: Ethyl Corporation, Richmond, Va.

[21] Appl. No.: 433,228

[22] Filed: Nov. 8, 1989

Related U.S. Application Data

[63] Continuation-in-part of Ser. No. 199,288, May 26, 1988, Pat. No. 4,900,856.

[51] Int. Cl.$^5$ ............................ C07F 3/00; C07F 3/02; C07F 3/06; C07F 5/06
[52] U.S. Cl. ................................ 260/665 G; 556/2; 556/118; 556/138; 564/138
[58] Field of Search ................. 260/665 G; 556/118, 556/2, 138; 564/138

[56] References Cited

U.S. PATENT DOCUMENTS

| | | | |
|---|---|---|---|
| 2,259,414 | 5/1953 | Davis | 260/429 |
| 2,655,524 | 10/1953 | Sowa | 260/448 |
| 2,671,812 | 3/1954 | Sparks et al. | 260/665 G X |
| 2,890,176 | 6/1959 | Ramsden et al. | 260/665 G |
| 3,396,192 | 8/1968 | Wendler et al. | 260/665 G |
| 3,418,369 | 12/1968 | Kauer | 260/665 G |
| 3,426,087 | 2/1969 | Ashby | 260/665 G |
| 3,444,199 | 5/1969 | Whitney | 260/665 G |
| 4,066,806 | 1/1978 | Speirs et al. | 427/253 |

OTHER PUBLICATIONS

Hatfield et al., Inorg. Chem., 1, 463, (1962).
Quagliano et al., J. Am. Chem. Soc., 92, 482, (1970).
Brun et al., C. R. Acad. Sci. t. 279, (Jul. 22, 1974), Series C–129.
Olah, *Friedel–Crafts and Related Reactions*, Interscience Publishers, New York, N.Y., (1963), vol. I, pp. 734–736.
Olah, *Friedel–Crafts and Related Reactions*, Interscience Publishers, New York, N.Y., (1963), vol. II, pp. 425–427.
R. M. Roberts et al., *Friedel–Crafts Alkylation Chemistry*, Marcel Dekker, New York, N.Y., (1984), pp. 673–676.
Isobe, M. et al., Chemistry Letters, Chemical Society of Japan, (1977), pp. 679–682.
Jacobson, Editor, *Encyclopedia of Chemical Reactions*, vol. V, Reinhold Publishing Corp., New York, 1953, p. 149.
Jacobson, Editor, *Encyclopedia of Chemical Reactions*, vol. VIII, Reinhold Publishing Corp., New York, 1959, p. 180.

Primary Examiner—Arthur C. Prescott
Attorney, Agent, or Firm—T. B. Morris

[57] ABSTRACT

A process for the preparation of an amine complex of a metal halide which comprises reacting said metal with an amine hydrohalide. The process can be extended to the use of metals such as aluminum, magnesium, zinc, iron, and the like.

19 Claims, No Drawings

PREPARATION OF METAL HALIDE-AMINE COMPLEXES

REFERENCE TO RELATED APPLICATIONS

This Application is a Continuation-in-Part of Application Ser. No. 199,288, filed May 26, 1988, now U.S. Pat. No. 4,900,85.

TECHNICAL FIELD

This invention pertains to the preparation of complexed metal salts. The metals in such salts may be aluminum, barium, calcium, cobalt, iron, magnesium, zinc, or the like. The anions in the salts are halides; preferably chloride, bromide, or iodide. The metal salts are complexed with an amine; in some instances, a tertiary amine is preferred. In addition to the components mentioned above (metal cation, anions, and amine) some compositions of this invention contain a hydrohalide (e.g. HCl). An example of a complex formed by the process of this invention is $AlCl_3 \cdot N(C_2H_5)_3$. Other complexes formed by this process include $ZnCl_2 \cdot 2N(C_2H_5)_3 \cdot HCl$, $MgCl_2 \cdot N(C_2H_5)_3$, and $FeCl_2 \cdot xN(C_2H_5)_3$.

BACKGROUND

According to Hatfield et al, (*Inorg. Chem.* 1, 463 (1962)), tertiary alkyl amines have little tendency to coordinate with metal salts unless stabilized by chelation. However, complexes of trimethylamine and/or triethylamine have been reported with halides of various metals including lithium, beryllium, aluminum, gallium, germanium, tin, etc. It is also stated by Hatfield et al that triethylamine does not react with calcium or zinc halides at 25° C. but gives stable 1:1 complexes with Co (II) halides.

Several transition metal complexes containing a monoquaternized tertiary diamine are known; Quagliano et al, *J. Am. Chem. Soc.*, 92, 482 (1970), and X-ray diffraction data are reported for the diquaternized tertiary diamine complexes of $ZnCl_2$ and $ZnBr_2$; Brun et al *C. R. Acad. Sci. Ser. C* 279, 129 (1974).

Olah, *Friedel-Crafts and Related Reactions*, Interscience Publishers, New York, N. Y. (1963) Volume I, pages 734–736, page 735 refers to the system: aluminum chloride-hydrogen chloride-toluene. On page 735, reference is also made to "red oils", e.g. 6.28 toluene $Al_2Br_6 \cdot HBr$. Other "red oils" are referred to on pages 734 and 736. Some amine complexes are discussed by Olah one pages 571 and 583. See Volume II, Pages 425–427 for a discussion of in situ preparation of metal halides.

Since 1886, it has been known that toluene disproportionates in the presence of aluminum chloride to form benzene and xylenes; R. M. Roberts et al, *Friedel-Crafts Alkylation Chemistry*, Marcel Dekker, New York, N. Y. (1984), Pages 673–676.

THE INVENTION

One embodiment of this invention is a process for preparing metal complexes. This embodiment can be exemplified by the following equation:

(1)
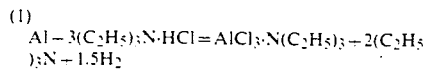

Another embodiment of the invention is exemplified by the following equation:

(2)
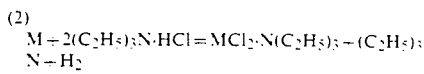

wherein M is Ba, Ca, Co, Fe, Mg, Zn, and the like, but not Al.

The amine within the amine hydrohalide reactant need not be a tertiary amine; it can be a primary or a secondary amine. However, tertiary amine-aluminum halide complexes produced by this invention are preferred. This is because they can be reacted with a metal hydride (such as $NaAlH_4$) to produce an amine alane. Tertiary amine alanes are useful intermediates for the preparation of silane, a valuable gas utilized in the preparation of semiconductor materials. Primary and secondary amines form unstable amine alanes which exist only at very low temperatures, e.g. below −40° C. Hence, reactions with primary and secondary amine alanes to form metal complexes may also have to be conducted at very low temperatures.

Other metal halide amine complexes of this invention can be reacted with metal alkyls to produce useful products. One such compound is tri-n-butylzinclithium prepared by reacting dichloro(N,N,N',N'-tetramethylethylenediamine)zinc ($TMEDA \cdot ZnCl_2$) with n-butyllithium. Tri-n-butyl-zinclithium is useful as a reagent in the preparation of $\alpha$, $\beta$-unsaturated carbonyl compounds. Intermediate metal halide amine complexes such as $MgCl_2 \cdot NEt_3$ may be useful as a source of dry $MgCl_2$ useful in preparing support materials for Ziegler and Ziegler-Natta catalysts. Additional uses for metal halide-amine complexes produced by the process of this invention are in electrochemistry, as halogenating agents, and in fluxes.

Reactions illustrated by the above equations can be catalyzed by the presence of a small quantity of aluminum halide. For example, in the process of Equation (1) aluminum chloride can be used as a catalyst. Furthermore, such reactions can be catalyzed by a complex comprising an aromatic hydrocarbon, amine, metal halide and a hydrohalide. Such complexes are formed during the course of the reaction between a metal such as aluminum, barium, calcium, iron, magnesium, zinc and the like, and a tertiary amine hydrohalide, such as triethylamine hydrochloride.

Reactions illustrated by the above equations are preferably conducted in the presence of an aromatic hydrocarbon. Such hydrocarbons form intermediate complexes with some of the reactants during the course of the reaction, and thereby enhance the progress of the process. Toluene is a preferred reaction medium for the following reasons. First, many metal halide-amine complexes produced by this invention are somewhat soluble in toluene or hot toluene, and toluene solutions of the complexes can be utilized per se in subsequent reactions (e.g. reaction with $NaAlH_4$). Secondly, the process of the invention proceeds well at the temperature of refluxing toluene. Thirdly, in many instances, technical grade amine hydrohalides employed as reactants in the process are contaminated with water, which may have a deleterious effect. It is convenient to remove any water impurity which is present by azeotroping with toluene before conducting the reaction.

It is surprising that little or no toluene undergoes disproportionation during the process. As mentioned above, toluene disproportionates when heated with a aluminum halide. Evidently, the presence of an amine prevents or significantly inhibits such disproportionation.

The process of this invention comprises an efficacious method for the formation of metal halides from Al, Ba, Ca, Co, Fe, Mg, Zn, and the like. When gaseous HCl is sparged into a toluene slurry of aluminum powder at 105°–110° C., aluminum chloride is produced, but the conversion of aluminum is only about 40–50 percent complete. A second phase comprising an $AlCl_3$·toluene·HCl complex is always formed, and this appears to inhibit the formation of the desired aluminum chloride product. In contrast, a process of this invention (namely the reaction of triethylamine hydrochloride with aluminum) catalyzed by 5 mole percent $AlCl_3$, proceeds in near-quantitative yield to produce $AlCl_3 \cdot N(C_2H_5)_3$.

The catalyst serves to reduce the induction period for the solid-solid reaction (between the metal and amine halide) from about 2 hours, to as little as about 15 minutes. The total cycle time can be as low as 2–2.5 hours. Accordingly, the process of this invention can be utilized to produce aluminum chloride in an aromatic hydrocarbon medium in a higher yield than obtainable by reacting Al and HCl. Furthermore, the process of this invention yields the aluminum chloride complex in an acceptable reaction time.

The process of this invention can be extended to produce such materials as:

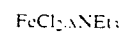

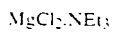

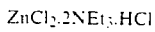

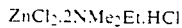

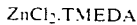

wherein $NEt_3$, $NMe_2Et$, and TMEDA are triethylamine, N,N-dimethylethylamine, and N,N,N',N'-tetramethylethylenediamine, respectively.

DESCRIPTION OF PREFERRED EMBODIMENTS

An embodiment of this invention is a process for the preparation of an amine complex of an aluminum trihalide, said process comprising reacting aluminum metal with an amine hydrohalide. In this process, the aluminum trihalide has the formula $AlX_3$; wherein X is a halide, preferably selected from chloride, bromide or iodide. Preferably, all three halide anions are the same. Of the anions, chloride and bromide are more preferred.

In another embodiment of this invention, an amine complex of a metal dihalide is formed. This process comprises reacting the metal with an amine hydrohalide such that a metal dihalide with the formula $MX_2$ is formed; wherein X is a halide, preferably selected from chloride, bromide or iodide. Preferably, both halide anions are the same. Of the anions, chloride and bromide are more preferred. Examples of metal dihalide complexes formed by the process of this invention include $ZnCl_2 \cdot$(TMEDA), $MgCl_2 \cdot NEt_3$, $FeCl_2 \cdot xNEt_3$, and the like.

The amine hydrohalide is preferably a hydrochloride or hydrobromide. The amine can be a primary, secondary, or tertiary amine. Furthermore, there may be one or more amino groups within the amine molecule. Thus, for example, the amines may be monoamines, diamines, triamines, and the like. Monoamines useful as hydrohalides in this invention have the formula $RNH_2$, $R_2NH$, and $R_3N$, respectively. In these formulas, the various radicals indicated by R may be alike or different. A wide variety of radicals are applicable. Preferred radicals are stable under the reaction conditions employed in this invention, i.e. they do not decompose or react to form an untoward amount of undesired coproduct. The amine hydrohalides for the process of this invention can be formed in situ or prepared separately.

It is preferred that the hydrocarbon radicals within the amines be common, simple hydrocarbon radicals, such as alkyl, alkylene, alicyclic or aryl. Of these radicals, alkyl and alkylene radicals are preferred. Most preferably, the amine has about 18 carbons or less.

As stated above, metal complexes formed by the process of this invention can be subsequently reacted to form amine alanes when aluminum is the metal reactant chosen. For the purpose of this invention, tertiary amines which form amine alanes are referred to herein as "complexing tertiary amines".

Suitable complexing tertiary amines which may be utilized in the invention are liquids or low melting solids and include tertiary aryl, alicyclic, alkyl, alkenyl and aralkyl amines, including monoamines, diamines, triamines, etc. Typically, the amines of the present invention may be N,N,N',N'-tetramethylethylenediamine, N,N-diphenylmethylamine, triethylenediamine, N-phenyl-N-methylethylamine, tricyclohexylamine, or mixtures thereof, and other similar compounds. A more preferred class of amines for use in the invention are aliphatic tertiary amines, which include trialkylamine and trialkenylamine. Further, these amines may generally contain up to about 30 carbon atoms each, and preferably contain alkyl and alkenyl groups each having from 1 to about 10 carbon atoms. Thus, useful amines of this class are tri-n-butylamine; tri-sec-butylamine; N,N-dibutylpentylamine; N-n-butyl-N-n-octyl-sec-butylamine; tripentylamine; trihexylamine; trihexenylamine; N,N-didecenylpentylamine; and the like, as well as mixtures thereof. Some unsaturation in the alkenyl amines may be reduced by the hydrogen produced in the process. A most preferred class of amines for use in the invention are those in the lower alkyl amines such as trimethylamine, triisopropylamine, and particularly, triethylamine. By the term "lower" is meant that the alkyl groups each contain 6 carbon atoms or less. The above compounds may be readily prepared by procedures well known to those skilled in the art. Products of the present invention are these amines complexed with aluminum halide.

Also usable complexing amines are the tertiary polyamines such as N,N,N',N'-tetramethylethylenediamine and 1,4-diazabicylco[2.2.2]octane. Other tertiary mono- and polyamines are suitable, such as tri-n-propylamine, triisopropylamine, N,N-dimethylethylamine, N,N-diethylmethylamine, tributylamine, N,N-dimethylpropylamine, N,N,N,',N'-tetramethyldiaminomethane, quinuclidine, methyl-1,4-diazabicyclo[2.2.2]octane, etc.

As indicated above, the complexing amines usable with the invention include the trialkylamines especially tri-loweralkylamines such as trimethylamine and triethylamine. Trimethylamine is a gas at room temperature and is therefore less convenient to use. Triethylamine is the most preferred complexing tertiary amine for this invention.

It has been discovered that when forming aluminum halide-amine complexes by the process of this invention, preferably about 3 moles of amine are employed for each 1 gram atom of aluminum metal used. (A reaction of this type is illustrated by Equation (1)). A modification of this reaction was tested in which all the amine would be consumed:

(2)
$$Al + (C_2H_5)_3N\cdot HCl + 2HCl = AlCl_3\cdot N(C_2H_5)_3 + 1.5H_2$$

This modification did not proceed well. The triethylamine tended to escape from the reaction zone and collect in the upper section of the reactor and reflux condenser. It was difficult to dislodge the amine from these locations. Furthermore, the yield of $AlCl_3\cdot N(C_2H_5)_3$ was only about 19 percent. This yield is much lower than the yields attainable when about 3 moles of amine are employed as exemplified by the process of Equation (1). For example, when triethylamine hydrochloride is reacted with aluminum according to the process of Equation (1), the conversion of aluminum is about 80 percent. Moreover, as stated above, when the process of that equation is conducted in the presence of about 5 mole percent aluminum chloride as a catalyst, the reaction proceeds in substantially quantitative fashion.

As stated above, the process of this invention is preferably conducted in the presence of a liquid aromatic hydrocarbon. Such materials assist contacting the solid aluminum metal with the solid amine hydrohalide. Furthermore, aromatic hydrocarbons form a liquid complex during the course of the process which facilitates contact between the reactants. Of the aromatic hydrocarbons, benzene, ethylbenzene, and the methyl substituted benzenes are preferred. As examples of such materials, one may use toluene, o-, m, and p-xylene, mesitylene, and the like. Mixtures of such materials may be employed. Tetralin is another applicable reaction medium.

The amount of aromatic hydrocarbon is not critical. Preferably, enough is employed to facilitate contacting the solid reactants. Thus, one preferably uses an amount of aromatic hydrocarbon which is suitable to provide a liquid reaction medium. As recognized by a skilled practitioner, the amount of aromatic hydrocarbon used for this purpose will vary within wide limits, depending upon such non-critical parameters as size of reaction vessel, stirring efficiency, etc. When an amount of aromatic hydrocarbon sufficient to function as a liquid reaction medium is used, there is usually sufficient aromatic hydrocarbon present to allow the reaction to proceed through formation of the complex or complexes formed in the process.

As indicated above, solvents are useful in the process of this invention. However, it is to be understood that the process can be conducted in the absence of a solvent. The amine hydrohalide complexes employed in the process are high melting materials, but ball-milling at temperatures above the melting point of the product metal halide-amine product could effect good contact between the reactants, and permit reaction to occur. For example, triethylamine hydrochloride melts at 253°–254° C., whereas aluminum chloride-triethylamine melts at 113°–114° C. Thus, the dry process might be run at temperatures above 115°–120° C. under moderate pressure, and the byproduct hydrogen and triethylamine vented off.

When the process of this invention is conducted in the presence of toluene and an aluminum halide-amine complex is being prepared, the initial reaction mixture usually comprises two solid phases and the liquid toluene. At the start of the reaction period, i.e. at or about the end of the induction period, a curd-like, solid phase begins to appear. This phase initially increases in amount and then diminishes to produce a heavy, second liquid phase.

After the curd-like solid phase has appeared, the new liquid phase is produced. This phase, which is insoluble in toluene, is heavier than the toluene reaction medium and appears to be a complex between the aluminum halide, toluene, amine, and HCl. If no aluminum halide catalyst is employed in the reaction mixture, an appreciable amount of the insoluble phase is still present at the completion of the run. Since this phase contains aluminum, not all of the starting aluminum is transformed into desired product. Thus, in the absence of aluminum halide catalysis, the conversion of starting aluminum, usually does not exceed about 80 percent.

When an aluminum halide catalyst is employed, the insoluble liquid phase also tends to disappear as the reaction proceeds, and at the end of the reaction it is substantially absent. Furthermore, the yield of desired product is much higher.

As stated above, it has been discovered that the toluene-insoluble, heavy liquid phase discussed above can serve as a catalyst for the reaction. Thus, a portion or all of the insoluble phase from a previous process run can be added as a catalyst to a subsequent run. When this expedient is employed, the heavy liquid phase will shorten the induction period from about 2 hours to about 30 minutes.

In order to use the insoluble phase as a catalyst, it is not necessary to isolate the heavy phase from a previous process run. Alternatively, the lighter phase can be separated, and the heavier phase left within the reaction vessel. Additional reactants can be added to the heavy phase and the reaction repeated. This repetition can be conducted several times until the volume of the reaction mass (including the heavy phase) begins to approximate the volume of the reaction vessel.

When the heavy, insoluble liquid phase is used as a catalyst, a catalytic amount, i.e. an amount sufficient to shorten the induction period, is employed. Thus, for example, from about 10 to about 50 weight percent or more of the reaction mass can be the toluene-insoluble phase.

The process of this invention is also catalyzed by metal halides. Typically, these metal halide catalysts have the formula $MX_y$ wherein M is a metal of the type which forms a complex by the process of this invention, X is a halide anion, and y is the valence of the metal cation. The metal may be, for example, aluminum, zinc, magnesium, or iron. The halide anions may be alike or different and are preferably selected from chloride, bromide or iodide; more preferably, chloride or bromide. Thus, for example, aluminum halides can be used to catalyze the process of this invention. In order to avoid or diminish complications in product workup and purification, the metal halide catalyst preferably contains the same metal which is used as the reactant. For the same reason, the metal halide catalyst preferably contains the same anion as the anion in the hydrohalide portion of the amine hydrohalide reactant. Consequently, when producing a aluminum halide-amine complex according to the process of this invention, aluminum chloride, aluminum bromide, and aluminum iodide are preferred catalysts, with the chloride and bromide being more preferred.

When a metal halide, such as a aluminum halide, is employed as a catalyst, a catalytic quantity is used. In other words, one uses enough metal halide to achieve a catalytic effect. Typically, from about 2 to about 12 mole percent aluminum halide is employed. Greater amounts can be used if desired. However, amounts of aluminum halide which substantially exceed 12 percent act as reactants rather than as catalysts, since the aluminum halide will react with other materials in the reaction system, e.g. the amine which is formed as a coproduct; confer Equation (1).

Metal halides are preferred catalysts for the process of this invention, since their use can result in substantially quantitative yield of metal halide-amine product. In contrast, as taught above, reaction conversions of about 80 percent or less are achieved when the toluene-insoluble complex is employed as a catalyst.

Mixtures of catalysts, and mixtures of the two types of catalysts can be used, if desired.

The process of this invention proceeds well at ambient pressure. It is not necessary to use atmospheric pressure, and higher or lower pressures can be used if desired.

The process of this invention proceeds well at mildly elevated temperatures. Generally speaking, a temperature above ambient is required to achieve reaction after an induction period of reasonably short duration, and to give a reasonable rate of reaction. Thus, for example, it is preferred to use the temperature of at least 50° C. More preferably, a temperature above about 75° C. is employed. The temperature should not be so high as to cause an unacceptable amount of undesirable side reaction(s). Thus, it is preferred that the reaction temperature be between about 75° C. and about 150° C., although higher or lower temperatures may be employed. The process proceeds well under toluene reflux at ambient pressure.

Tests for the effect of temperature on reaction rate showed that operation at 80° C. gave an 88.5 percent conversion of aluminum in 4.5 hours with an induction period of 180 minutes. Higher temperatures, e.g. 140° C., in refluxing xylene gave a 45 minute induction period, but the time required for complete consumption of aluminum was about 2.5 hours. Preparation of the aluminum chloride adduct with trimethylamine required considerably more time than for production of the homologous triethylamine adduct. Instead of the 2–2.5 hours normally required to prepare the triethylamine adduct, about 12 hours were required to prepare the trimethylamine adduct in comparable yield.

The reaction time is not a truly independent variable, and is dependent at least to some extent on the nature of the reactants and the other reaction conditions employed. Thus, as indicated above, reaction with trimethylamine hydrochloride takes a considerably longer time than with triethylamine hydrochloride. Also, finely divided aluminum powder reacts more quickly than coarse wire ends.

As stated above, the reaction time comprises an induction period before reaction initiates. The length of the induction period depends to some extent on the reaction temperature and whether a catalyst is employed in the reaction mixture.

Without a catalyst, reaction of aluminum with triethylamine hydrochloride may entail an induction period of up to about 2 hours. If aluminum chloride is used as a catalyst at a similar temperature (110°–115° C.) the induction period can be shortened to about 30 minutes. When a catalyst is employed, the entire reaction cycle when aluminum is reacted with triethylamine hydrochloride can be about 2 hours. On the other hand, in a non-catalyzed system, reaction time (induction period plus reaction period) can be about 4 hours. Thus, in general, reaction times for the process of this invention are generally within a period of from about 1.5 to about 10 hours.

EXAMPLE A

In the process of this example, aluminum chloride is produced by reacting aluminum powder and hydrogen chloride in toluene.

A 100-mL round bottom flask was fitted with a reflux condenser and a Teflon feed line for gaseous HCl, a magnetic stirrer, and a nitrogen bubbler. To the flask was charged 0.20 gram of aluminum powder and 50.0 grams of toluene. The slurry was heated to reflux (110 C.) and the hydrogen chloride was sparged into the slurry. After 10 minutes color began to appear, and the color gradually changed from yellow to orange. After 1 hour and 10 minutes, the solution seemed to be clear; and accordingly, the hydrogen chloride feed was stopped and the reaction mixture was cooled. At room temperature, an orange oil was present at the bottom of the flask, and the toluene layer above was somewhat yellow.

The toluene layer above was heated again with a distillation head on the flask to remove dissolved HCl. About 3 mL of toluene distillate were obtained. The flask was cooled in ice water and 0.80 gram of triethylamine was slowly added to form the aluminum chloride-triethylamine adduct. The toluene turned from brown to yellow almost instantly upon adding the triethylamine. Analysis of the toluene solution for aluminum and chloride showed the conversion of aluminum to $AlCl_3$ to be 43%.

When the reaction is conducted in this manner, i.e. preparation of aluminum chloride with subsequent reaction with triethylamine, the conversion of aluminum is about 40-50 percent.

EXAMPLE 1

Preparation of Triethylamine Complex of Aluminum Chloride

To a 100-mL round bottom flask was added 6.45 grams of triethylamine hydrochloride ($Et_3N \cdot HCl$) (98%, 0.045 mole) and 60 grams of toluene. About 9.1 grams of toluene was distilled from this mixture to remove any water that was present as an impurity. The distillate was cloudy, indicating that water was removed from the reaction zone. Apparently, the water was introduced with the hygroscopic triethylamine hydrochloride.

After the removal of water by azeotroping with toluene as mentioned above, 0.40 gram of aluminum powder (0.015 gram atom) was added to the reaction flask. The mixture was stirred well while refluxing, using a 120 C. oil bath as the source of heat.

No visible sign of reaction was noted for about 1 hour, then curd-like solids began to appear. After 3 hours, the reaction slurry noticeably cleared. At 5 hours, no curd-like material appeared to be present; however, some aluminum metal was present at the bottom of the reaction flask and two liquid phases. The upper phase was yellow and the lower, heavier liquid phase a dark orange in color. The flask was cooled and the liquid phases separated. The upper phase weighed 52.3 grams and the lower phase 2.1 grams. Analysis of the upper phase showed an aluminum content of 0.4 percent and a chloride content of 1.62 percent. This represents an aluminum to chlorine atomic ratio of 1:3.08. The lower phase had an aluminum content of 5.09 percent and a chloride content of 25.6 percent. This corresponds to an aluminum/chlorine ratio of 1:3.85. Apparently, the upper phase contains aluminum chlo- Generally, no change was immediately noted in the slurry. After an induction period, curd-like solids gradually appeared and liquified to a dark gray, heavy, toluene-immiscible phase. The induction period varied from 15 minutes to about 2 hours, depending on the type of aluminum (powder or wire ends) and whether a catalyst was present. Catalyzed reactions extended for about 2–2.5 hours before the heavy bottom phase disappeared and a homogeneous solution remained. Conversion of aluminum to aluminum chloride was determined by analysis of the toluene solution for soluble aluminum and chloride. Results are shown in Table I.

TABLE I

| Run | Aluminum | Solvent | Catalyst | Induction Period (Minutes) | Temperature (°C.) | Reaction Time (Hrs.) | Conversion %* Al | Cl | Ratio Cl/Al |
|---|---|---|---|---|---|---|---|---|---|
| Synthesis of AlCl$_3$·N(C$_2$H$_5$)$_3$ | | | | | | | | | |
| 1 | a | Toluene | AlCl$_3$ | 30 | 110 | 2 | 88.5 | — | — |
| 2 | b | Toluene | AlCl$_3$ | 60 | 110 | 2.5 | 98 | 102 | 3.1 |
| 3 | b | Xylene | AlCl$_3$ | 45 | 140 | 2.5 | 97 | 106 | 3.1 |
| 4 | a | Toluene | AlCl$_3$ | 180 | 80 | 4.5 | 88.5 | 98 | 3.1 |
| 5 | a | Toluene | None | 75 | 110 | 3 | 92.5 | 100 | 3.2 |
| Synthesis of AlCl$_3$·N(CH$_3$)$_3$ | | | | | | | | | |
| 6 | b | Toluene | AlCl$_3$ | 240 | 110 | 12 | 90 | 100 | 3.1 | a — Aluminum powder; 90 percent less than 325 mesh.
b — One mm diameter aluminum wire ends.
* — To toluene-soluble AlCl$_3$. Values above 100% reflect uncertainty in purity of starting (C$_2$H$_5$)$_3$N·HCl ride with a slight amount of hydrogen chloride. The lower phase appears to be aluminum chloride-HCl complexed with toluene and triethylamine. The overall conversion of aluminum to AlCl$_3$ (in both phases) was 80 percent.

The inability of the triethylamine hydrochloride to completely deplete the aluminum appears to be associated with the toluene-immiscible complex. When the complex was repeatedly cycled with fresh reactants, its mass progressively increased, but the yield of toluene-soluble AlCl$_3$·N(C$_2$H$_5$)$_3$ remained constant. Operation under distillation conditions where the excess triethylamine was steadily removed did not prevent formation of the immiscible complex nor increase the conversion of aluminum to aluminum chloride-triethylamine product.

An advantage to the direct production of the amine complex according to the above example, when compared to the stepwise process reported in Example A, is that no disproportionation of toluene occurs. In the absence of triethylamine, about 2 percent of the toluene is converted to benzene, xylene, and trimethylbenzene.

EXAMPLE 2

Catalytic Preparation of Triethylamine Complex of Aluminum Chloride

In a typical reaction, 6.32 grams (0.045 mole) of 98 percent triethylamine hydrochloride and 50 grams of dry toluene were placed in a 100-mL round bottom flask, equipped with a stirring bar, and a short-path length distilling head and receiver attached. About 20 grams of toluene was distilled from the mixture to remove water as an azeotrope; the water entering into the reaction zone with the hygroscopic amine hydrochloride. Then, about 0.41 gram (0.015 gram atom) of aluminum powder, or 1 mm diameter aluminum wire ends and 0.10 gram aluminum chloride catalyst (0.75 millimole) were added. A reflux condenser was attached, and the flask immersed in a 130° C. oil bath and stirred magnetically.

The procedure of the above example can be repeated using a reaction temperature of from about 75.C to about 150 C. In a manner similar to the process as reported above, the analogous amine hydrobromides can be used in place of the amine hydrochlorides employed. In a similar manner, the processes can be conducted in the presence of benzene, ethylbenzene, o-, m-, p-xylene, or a mixture thereof, or mesitylene. The process can be repeated using from about 2 to about 12 mole percent aluminum chloride or aluminum bromide catalyst.

The procedure of the above example can be used with other "complex tertiary amines" such as those named above.

It has been demonstrated that the process of this invention can be extended to other metals besides aluminum. Three syntheses were carried out using magnesium metal in the form of turnings and powder. The reactions were conducted in boiling toluene for 8–10 hours each. One run included glass beads in the reactor to provide some degree of attrition for the solid-solid reaction.

The process of this invention has also been extended to the preparation of a 1:1 complex of zinc chloride with N,N,N',N'-tetramethylethylenediamine (TMEDA) and ZnCl$_2$·2NMe$_2$Et·HCl. The tertiary diamine complex of zinc chloride is known and has been used to prepare LiZnR$_3$ compounds wherein R is alkyl: Isobe et al, *Chem. Lett.* 1977, 679. The lithium zinc alkyls are good reagents for conjugate addition to alpha, beta unsaturated carbonyl compounds.

Examples 3 through 7 illustrate the process of this invention with metals such as zinc, magnesium, and iron.

EXAMPLE 3

Preparation of Triethylamine Complex of MgCl$_2$

To a 100-mL round-bottomed flask was added about 6 grams of Et$_3$N·HCl and 50 grams of toluene. After removing water by azeotropic distillation of the toluene, about 31 grams of toluene remained in the flask. To the flask was added about 10 mg of AlCl3 catalyst and about 0.55 grams magnesium turnings. A reflux condenser and nitrogen bubbler were attached to the flask. The flask was heated for 4 hours using a 120 to 125 C. hot oil bath, then cooled. The next day the flask was heated for eight hours using a 130° to 135° C. hot oil bath. About 30 grams of the toluene phase was decanted off. The solids remaining weighed about 7 grams. The solids were dissolved in 60 grams of distilled water and unreacted Mg was filtered off. After rinsing with 20 mL of water, the Mg was oven-dried and weighed about 0.38 grams. Analysis showed about 31% conversion of Mg to $MgCl_2$.

EXAMPLE 4

Preparation of Triethylamine Complex of $ZnCl_2$

To a 100-mL round-bottomed flask was added about 6 grams of $Et_3N \cdot HCl$ and 50 grams of toluene. A short-path distillation head was attached and about 16.2 grams of toluene and water was collected in the distillate when heated in a 130° C. hot oil bath. About 2 grams of zinc powder (98%, 0.030 mole) was added to the resulting slurry and a reflux condenser was attached to the flask. The flask was heated in a 125° to 130° hot oil bath. After 2½ hours, most of the solids were gone and there was a colorless second liquid phase. This second phase solidified into a white solid on cooling. About 35 grams of the lighter toluene phase was decanted off. After drying the residue at 50°–60° C., about 4 grams of white solids was collected. Nuclear magnetic resonance (NMR) analysis showed the composition to be comprised of a 1:1 mixture of $ZnCl_2 \cdot N(C_2H_5)_3$ and triethylamine hydrochloride. This amounted to about 60% conversion of Zn to $ZnCl_2 \cdot N(C_2H_5)_3$.

EXAMPLE 5

Preparation of the TMEDA Complex of $ZnCl_2$

To a 100-mL round-bottomed flask was added about 5 grams of trimethylamine hydrochloride (98%, 0.05 mole) ($Me_3N \cdot HCl$) about 3 grams of N,N,N',N'-tetramethylethylenediamine (TMEDA) (99%, 0.028 mole) and about 50 grams of dry toluene. The flask was fitted with a short-path distillation head and immersed in a 130° C. oil bath to remove any water impurities by azeotropic distillation and exchange ligands according to the following equation:

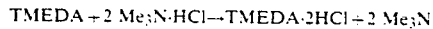

The mixture was refluxed for 45 minutes and about 3 mL of distillate were collected. Left in the round-bottomed flask was a fine white precipitate, and dry toluene.

The mixture was cooled and about 1.5 grams of zinc powder (99%, 0.025 mole) was added. The flask was fitted with a reflux condenser cooled with ice water, and nitrogen bubbler and immersed in the 135° C. oil bath. The toluene was refluxed for 1 hour and 45 minutes, then held overnight under a nitrogen pad. Before cooling the flask, a clear, colorless heavy second phase was evident at the bottom of the mixture. Three days later, the oil bath was heated to 135° C. and the toluene was refluxed another 1 hour and 15 minutes for a total of 3 hours. The final mixture was a water-white single phase, which indicated that the TMEDA-$ZnCl_2$ complex was soluble in hot toluene to at least 12% (6.4 grams in about 50 grams toluene).

The product mixture was allowed to cool to room temperature (about 26° C.). White needles crystallized out and were filtered off. The filter cake was rinsed with 20 mL of n-pentane and vacuum dried (10 mm Hg at 80° C.) for 1 hour. About 6 grams of white crystals was collected. Analysis of the crystals showed the complex to contain about 25% Zn and about 28% Cl which represents about a 93% yield and about 98% purity.

EXAMPLE 6

Preparation of Triethylamine Complex with Mg $Cl_2$

To a 100-mL round-bottomed flask was added about 6 grams $Et_3N \cdot HCl$ and 50 grams toluene. The mixture was distilled using a hot oil bath to remove water as an azeotropic mixture with toluene, and the remaining toluene in the flask weighed about 30 grams. About 0.5 grams Mg powder and 10 grams of glass beads (6–8 mm diameter) were added to the flask. A reflux condenser and nitrogen bubbler was attached to the flask and the flask was heated in a 130° to 135° C. hot oil bath for 5 hours while stirring. After about 15 minutes, curd-like solids appeared. The next day, the flask was heated in a 135° C. hot oil bath for 5 hours and then cooled and the solids filtered and rinsed with 25 mL of dry toluene. The solids were dried under partial vacuum for 2 hours at 60° C. The dry tan-colored solids weighed about 4 grams. X-ray diffraction (XRD) analysis showed about 60% conversion of Mg to $MgCl_2$.

EXAMPLE 7

Preparation of Triethylamine Complex of $FeCl_2$

To a 100-mL round-bottomed flask was added about 6 grams of $Et_3N \cdot HCl$ and about 50 grams of toluene. Water present was distilled off with the toluene as an azeotrope. The residue weighed about 30 grams and about 27 grams of distillate was collected. About 1 gram of iron powder (98%, 0.022 mole) was then added to the residue in the flask. A reflux condenser was fitted to the flask with a attached nitrogen bubbler and the flask was placed in a 135° C. oil bath and heated for 3.5 hours while stirring with a magnetic stirrer. After 30 minutes a curd-like solid appeared. At the end of the heating time, the white solid had become a hard mass. After standing overnight, the toluene was decanted off and replaced with about 36 grams of diglyme. The reflux condenser was reinstalled and the flask was heated in a 135° to 160° C. hot oil bath for 3 hours while stirring. Grey solids appeared. The flask was cooled, and the contents were dumped into 400 mL of water. A green floc (probably $Fe(OH)_2$) formed. HCl was added to clarify the mixture. The aqueous phase weighed about 435 grams. Analysis showed about 58% conversion of Fe to $FeCl_2 \cdot NEt_3$.

Surprisingly, magnesium was attacked comparatively slowly by triethylamine hydrochloride, even when attrition stirring was employed. The product, $MgCl_2 \cdot N(C_2H_5)_3$ was afforded in 30–60 percent conversion in three runs. Being largely insoluble in toluene, the complex salt product was recovered admixed with unreacted magnesium and triethylamine hydrochloride. It may be possible to drive the reaction to completion by ball-milling the solids, at least in the later stages of the process.

Zinc powder reacted much more readily than magnesium, even though the product $ZnCl_2 \cdot N(C_2H_5)_3$ was insoluble in toluene. This complex salt was produced as a clear liquid in hot toluene and solidified to a white solid when cooled. The isolated complex melted at 127°–130° C. with decomposition indicative of ready dissociation and loss of amine.

Table II summarizes the results of the preparation of various metal amine complexes other than aluminum.

TABLE II

Synthesis of Metal Chloride-Amine Complexes

| Run | Metal | Solvent | Catalyst | Temperature (°C.) | Reaction Time (Hrs.) | Conversion %*** | Product |
|---|---|---|---|---|---|---|---|
| 1 | Mg* | Toluene | $AlCl_3$ | 110 | 12 | 30 | $MgCl_2 \cdot NEt_3$ |
| 2 | Zn | Toluene | None | 110 | 2.5 | 60 | $ZnCl_2 \cdot 2NEt_3 \cdot HCl$ |
| 3 | Mg** | Toluene | None | 110 | 8 | ~50 | $MgCl_2 \cdot NEt_3$ |
| 4′ | Mg** | Toluene | None | 110 | 10 | 60 | $MgCl_2 \cdot NEt_3$ |
| 5 | Fe | Toluene Diglyme | None | 110 160 | 6.5 | 58 | $FeCl_2 \cdot xNEt_3$ |

*Turnings.
**Reade Powder.
***Based on the metal charged.
Attrition Agitation.

I claim:

1. Process for the preparation of an organic amine complex of a metal halide, other than aluminum halide, said process comprising reacting a reactant mixture composed of the metal and an organic amine hydrohalide selected from a primary organic amine hydrohalide, a secondary organic amine hydrohalide, and a tertiary organic amine hydrohalide.

2. The process of claim 1 wherein the halide ions within the metal halide are chloride, bromide, or iodide.

3. The process of claim 1 catalyzed by a catalytic quantity of metal halide wherein the metal in the metal halide is Al, Fe, Mg, or Zn.

4. The process of claim 1 wherein the metal is Ba, Ca, Co, Fe, Mg, or Zn.

5. The process of claim 1 being conducted in the presence of an aromatic hydrocarbon.

6. The process of claim 5 wherein the aromatic hydrocarbon is toluene.

7. The process of claim 5 being catalyzed by a catalytic quantity of a toluene-insoluble complex of toluene-amine-hydrogen halide-metal halide produced in a previous process run in which the metal and an organic amine hydrohalide were reacted with each other in a toluene reaction medium.

8. The process of claim 6 being conducted at toluene reflux temperature.

9. The process of claim 6 wherein the reactant mixture contains a water impurity and wherein the water impurity in the reactant mixture is removed from the reaction zone by forming an azeotrope with toluene which is distilled and removed in the distillate.

10. The process of claim 1, wherein said amine is a tertiary amine.

11. Process for preparation of an organic amine complex of zinc halide, said process comprising reacting a reactant mixture composed of zinc and an organic amine hydrohalide selected from a primary organic amine hydrohalide, a secondary organic amine hydrohalide, and a tertiary organic amine hydrohalide.

12. The process of claim 11 wherein the halide ions within the metal halide are chloride, bromide, or iodide.

13. The process of claim 11 catalyzed by a catalytic quantity of metal halide wherein the metal in the metal halide is Al, Fe, Mg, or Zn.

14. The process of claim 11 being conducted in the presence of toluene and at toluene reflux temperature.

15. The process of claim 11 wherein the amine is a tertiary amine.

16. The process of claim 14 wherein the reactant mixture contains a water impurity and wherein the water impurity in the reactant mixture is removed from the reaction zone by forming an azeotrope with toluene which is distilled and removed in the distillate.

17. The process of claim 14 being catalyzed by a catalytic quantity of a toluene-insoluble complex of toluene-amine-hydrogen halide-zinchalide pro in a previous process run in which zinc and an organic amine were reacted with each other in a toluene reaction medium.

18. A composition of matter having the formula $MX_y \cdot YA \cdot ZHX$ wherein M is magnesium, or iron. X is a chloride or bromide ion; y is the valence or the metal M; Y is 1 or 2; A is an amine; and Z is 0, 1 or 2.

19. The composition of claim 18 having the formula $MgCl_2 \cdot NEt_3$ where Et is ethyl.

* * * * *